US011033701B2

(12) United States Patent
Navarijo

(10) Patent No.: US 11,033,701 B2
(45) Date of Patent: *Jun. 15, 2021

(54) BAG/VALVE/MASK RESUSCITATOR STABILIZER ARM AND METHOD OF USE

(71) Applicant: EMENDARE INNOVATIONS, LLC, San Antonio, TX (US)

(72) Inventor: Craig S. Navarijo, San Antonio, TX (US)

(73) Assignee: EMENDARE INNOVATIONS, LLC, San Antonio, TX (US)

( * ) Notice: Subject to any disclaimer, the term of this patent is extended or adjusted under 35 U.S.C. 154(b) by 258 days.

This patent is subject to a terminal disclaimer.

(21) Appl. No.: 16/030,438

(22) Filed: Jul. 9, 2018

(65) Prior Publication Data

US 2018/0318533 A1 Nov. 8, 2018

Related U.S. Application Data

(63) Continuation of application No. 14/510,740, filed on Oct. 9, 2014, now Pat. No. 10,016,570.

(51) Int. Cl.
*A61M 16/00* (2006.01)
*A61M 39/10* (2006.01)
(Continued)

(52) U.S. Cl.
CPC .... *A61M 16/0084* (2014.02); *A61M 16/0075* (2013.01); *A61M 16/0078* (2013.01);
(Continued)

(58) Field of Classification Search
CPC .............. A61M 16/00; A61M 16/0045; A61M 16/0048; A61M 16/0057; A61M 16/0075;
(Continued)

(56) References Cited

U.S. PATENT DOCUMENTS 3,196,866 A * 7/1965 Adams .............. A61M 16/0078
128/205.13
3,473,529 A 10/1969 Wallace
(Continued)

FOREIGN PATENT DOCUMENTS

DE 102005001942 7/2006

OTHER PUBLICATIONS

Supplementary European Search Report Issued in Corresponding European Application No. 15849029.2, dated May 4, 2018.

*Primary Examiner* — Colin W Stuart
(74) *Attorney, Agent, or Firm* — Norton Rose Fulbright US LLP

(57) ABSTRACT

A stabilizer arm for a BVM resuscitator and method of use is disclosed. The stabilizer arm provides the necessary support to the reservoir bag to enable the user to exert downward pressure on the BVM resuscitator while simultaneously squeezing the reservoir bag, and creates force that is focused, directed, and realized at the mask of the assembly. Due to the presence of the stabilizer arm, this pressure pushes the facial mask downward to assist in forming a tight mask to face seal. The stabilizer arm may be internal, external or integrated into the reservoir bag wall of the BVM resuscitator and may be retro-fitted or original equipment manufactured. The external stabilizer arm may be designed to engage the outlet port neck of the BVM resuscitator with an open collar or a closed collar. The internal stabilizer arm may be configured to fit BVM resuscitators having single piece or multiple piece outlet valve design.

18 Claims, 15 Drawing Sheets

(51) Int. Cl.
*A61M 16/08* (2006.01)
*A61M 16/20* (2006.01)

(52) U.S. Cl.
CPC ..... *A61M 16/0048* (2013.01); *A61M 16/0081* (2014.02); *A61M 16/0816* (2013.01); *A61M 16/0875* (2013.01); *A61M 16/20* (2013.01); *A61M 16/208* (2013.01); *A61M 2039/1033* (2013.01); *A61M 2205/07* (2013.01); *A61M 2205/071* (2013.01); *A61M 2205/075* (2013.01); *A61M 2205/586* (2013.01); *A61M 2209/08* (2013.01)

(58) Field of Classification Search
CPC .......... A61M 16/0078; A61M 16/0081; A61M 16/20; A61M 16/208; A61M 16/0084; A61M 16/0497; A61M 16/06; A61M 16/08; A61M 16/0816; A61M 16/0875; A61M 39/10; A61M 2039/1027; A61M 2039/1033; A61M 2039/1038; A61M 2205/07; A61M 2205/071; A61M 2205/075; A61M 2205/586; A61M 2209/08
See application file for complete search history.

(56) References Cited

U.S. PATENT DOCUMENTS

| | | | | |
|---|---|---|---|---|
| 3,859,997 | A | * | 1/1975 | Douma ............. A61M 16/0078 128/205.17 |
| 3,882,860 | A | | 5/1975 | Frimberger |
| 4,484,577 | A | | 11/1984 | Sackner et al. |
| 4,898,166 | A | * | 2/1990 | Rose ................. A61M 16/0078 128/205.13 |
| 5,163,424 | A | | 11/1992 | Kohnke |
| 5,222,491 | A | * | 6/1993 | Thomas ............ A61M 16/0084 128/205.13 |
| 5,359,998 | A | | 11/1994 | Lloyd |
| 5,540,221 | A | | 7/1996 | Kaigler et al. |
| 5,558,371 | A | | 9/1996 | Lordo |
| 5,996,579 | A | | 12/1999 | Coates et al. |
| 10,016,570 | B2 | * | 7/2018 | Navarijo ........... A61M 16/0078 |
| 2001/0029950 | A1 | | 10/2001 | Haubeil |
| 2003/0213486 | A1 | | 11/2003 | Wang |
| 2008/0087285 | A1 | | 4/2008 | Kuo |
| 2008/0257351 | A1 | | 10/2008 | Gitschlag |
| 2009/0071482 | A1 | | 3/2009 | Huddlestone |
| 2010/0087760 | A1 | | 4/2010 | Thompson et al. |
| 2011/0120472 | A1 | | 5/2011 | Lee et al. |
| 2016/0101252 | A1 | * | 4/2016 | Navarijo ........... A61M 16/0084 128/202.27 |

* cited by examiner

BAG/VALVE/MASK RESUSCITATOR STABILIZER ARM AND METHOD OF USE

CROSS-REFERENCE TO RELATED APPLICATIONS

This application is a continuation of U.S. patent application Ser. No. 14/510,740, filed Oct. 9, 2014, the contents of which is incorporated into the present application by reference.

BACKGROUND OF THE INVENTION

1. Field of the Invention

The present invention relates generally to improvements in bag valve mask resuscitators. Specifically, the present invention relates to internal and external stabilizer arms for bag valve mask resuscitators.

2. Description of the Related Art

Bag valve mask (hereinafter BVM) resuscitators are commonly used in emergency care and critical care situations. When used in the field, BVM resuscitators deliver air under positive pressure to a patient not then capable of breathing independently. The BVM resuscitator commonly known in the art is a manually-operable, deformably-resilient, football-shaped bag formed from a ribbed, flexible thermoplastic which includes an air intake valve at one end and a breathing/exhaust valve at the other end to which a mask to cover the nose and face is affixed or operably connected.

Present BVM resuscitators have design deficiencies which create challenges for the user. One such deficiency is the "softness" or collapsibility of the reservoir bag that is squeezed to create pressure and ventilate the patient. Present BVM resuscitators have reservoir bags constructed most commonly from silicone or the like, that collapse or fold and do not tolerate downward pressure from the hand operating the bag, thereby limiting the user to establishing and maintaining the mask-to-face seal with a single hand placed around the mask and face of the patient.

Moreover, this circumferential seal must be made between the non-breathing patient's facial skin and the mask of the BVM resuscitator while simultaneously maintaining an open airway by keeping the patient's head in a constantly tilted position, all with a single hand. Thus, this collapsibility or folding of the reservoir bag, coupled with a problematic seal of the mask around the mouth and nose, frequently causes difficulty or outright inability to achieve a consistently tight seal for a single user. The absence of a tight seal permits the pressurized air to follow the path of least resistance, leaking out of the mask, thereby resulting in insufficient ventilation of the patient.

A tight seal around the mask is much more easily attained, of course, when both hands are used to create pressure on opposite sides of the mask. Pressure exerted on the mask with both hands can more easily be controlled and adjusted to compensate for anatomical differences and any other reasons for poor seal. However, the use of two hands by the provider to apply pressure on the mask portion of the BVM resuscitator means that a second provider has to squeeze the bag in order for the unit to work. This unnecessarily consumes valuable manpower that could be utilized to perform other potentially lifesaving measures.

Thus, there is a need in the art for an improved BVM resuscitator which would allow the user's "bagging hand" to apply downward force while simultaneously squeezing the reservoir bag, effectively allowing both hands to make the seal. The bagging hand would be allowed to fully squeeze the reservoir bag as normal. Such a device would successfully allow a single provider to use both hands to create the necessary mask-to-face seal while simultaneously squeezing the bag to create and maintain the necessary seal to more effectively ventilate the non-breathing patient.

SUMMARY OF THE INVENTION

The present invention discloses a stabilizer arm for a BVM resuscitator and method of use. The stabilizer arm provides the necessary support to the BVM resuscitator to enable the user to exert downward pressure on the bag while simultaneously squeezing it. Due to the presence of the stabilizer arm, this pressure also pushes the facial mask downward to assist in forming a tight mask to face seal. Multiple embodiments of the stabilizer arm are disclosed. The stabilizer arm may be internal, external, or constructed into the material of the reservoir bag of the BVM resuscitator and may be retro-fitted or original equipment manufactured. The external stabilizer arm may be designed to engage the neck of the outlet port of the BVM resuscitator with an open collar or a closed collar configuration. The internal stabilizer arm may be configured to fit BVM resuscitators having a single piece or multiple piece outlet valve design.

The external embodiment of the retro-fitted device is a rigid bar preferably shaped to the curvature of the reservoir bag having a member such as a curved hook that can attach around the valve of the BVM resuscitator. In other embodiments, the bar is not necessarily curved, but has a shape compatible with the BVM resuscitators currently in use so as to allow the stabilizer bar to rest close to or on the outer surface of the bag portion of the BVM resuscitator. The connective valve (between the bag and mask) portion of present BVM resuscitators is constructed from a harder plastic than the softer reservoir bags. This hard plastic region can serve as an anchoring point for the external stabilizer bar to attach and extend along the bag for the bagging hand to rest on and apply downward pressure.

The connecting member of the stabilizer bar would reach around the neck of the valve portion of the BVM resuscitator, forming a fulcrum and causing the valve portion to act as a support for the stabilizer bar. The hard plastic valve region would be pulled upward, bracing the stabilizer bar in place and preventing downward pressure from the bagging hand to affect the shape or functionality of the bag. Simultaneously, this downward pressure would then transfer to the mask or seal of the BVM resuscitator on the opposite side of the mask from the hand presently holding the mask in place. This new ability to create opposing pressure on the mask would allow a single user to functionally create a seal which is equivalent to that produced by the two-person technique (the two person technique utilizes one provider to form the seal using two hands to hold the mask in place, and a second provider to squeeze the bag).

Although the bagging hand is at an elevated position to the mask holding hand, the resulting downward pressure enabled by the new device is transferred to the bottom of the mask where the "seal" is necessary. This ability to generate pressure from the raised, bagging hand at the point of the seal resolves the difficulty a single BVM resuscitator user has in creating and maintaining the necessary seal. The new device improves the efficacy of the BVM resuscitator, reduces the manpower required to effectively ventilate a patient in need, and allows healthcare providers to more easily and timely create and maintain the necessary seal. The stabilizer bar of the present invention allows a single provider to readily establish the necessary seal, and more importantly, to maintain the seal more easily than the BVM resuscitators currently in use.

This external retro-fitted stabilizer bar may be of variable dimensions, shapes, and materials and may simply hook snugly around the neck of the valve portion of the BVM resuscitator or may be secured in place by various means including but not limited to a snap closure.

The retro-fitted stabilizer bar may also be internally fitted within the reservoir bag of the BVM resuscitator. The internal embodiment of the retro-fitted stabilizer bar is configured to fit BVM resuscitator bags having multiple piece outlet valve construction. In this embodiment, the stabilizer bar is a rigid bar coming to rest against or near the reservoir bag having a stabilizer ring that can attach to the valve connector tube of the BVM resuscitator.

In another preferred embodiment, the internal stabilizer bar may be original equipment manufactured and configured to fit BVM resuscitator bags having single piece outlet valve construction. With original equipment manufactured designs, the rigid bar may be additionally reinforced and of a larger size than that of the retro-fitted version. In these embodiments, the stabilizer bar may be molded as one piece with the outlet valve. Alternately, the outlet connector tube of the outlet valve may be designed to attach to the stabilizer ring of the stabilizer bar. The stabilizer bar may be securely attached to the outlet valve via snap-on, twist and lock, screw attachment, glue/cement, or other connective or more permanent assemblies known in the art.

Various alternate embodiments of the stabilizer arm include an angled or extended arm with attached lever. Such designs may be fixed or articulated. Other embodiments include double or multiple stabilizer arm designs, both internal and external to the reservoir bag or built into the actual body of the bag. The stabilizer bar may be lengthened or shortened in various alternate embodiments including but not limited to folding, telescoping, sliding, or snapping. This would allow the device to be extended to fit reservoir bags of varying size and to be stored in a compact space when not in use.

DETAILED DESCRIPTION OF THE PREFERRED EMBODIMENTS

Figure 1:
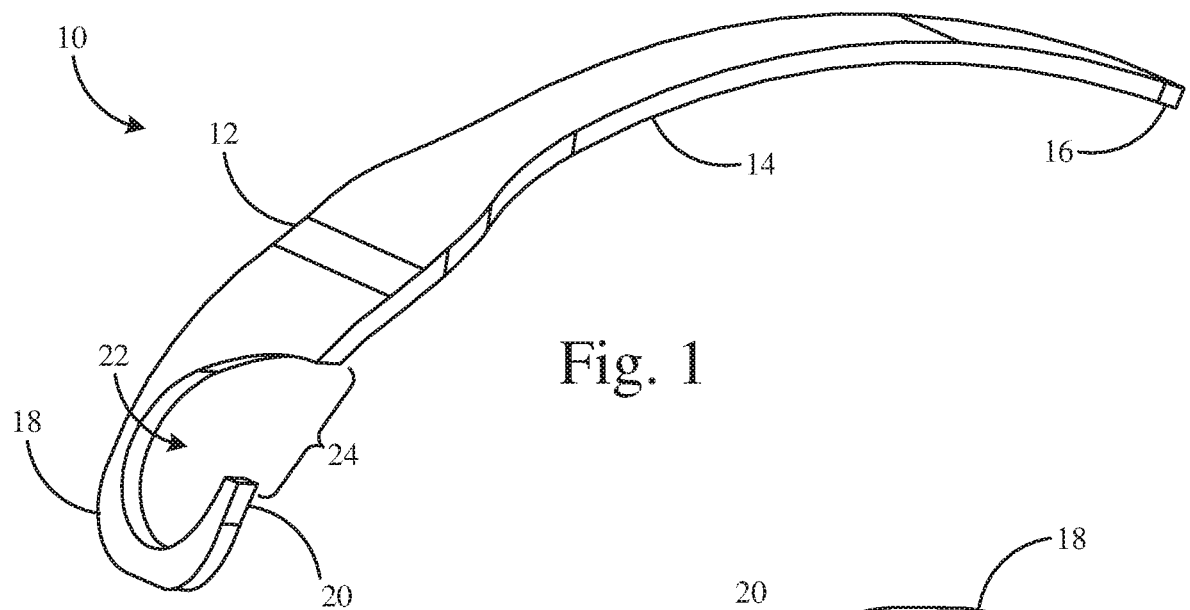
FIG. 1 is a perspective view of a first preferred embodiment of the retro-fitted external stabilizer bar of the present invention.
Figure 2:
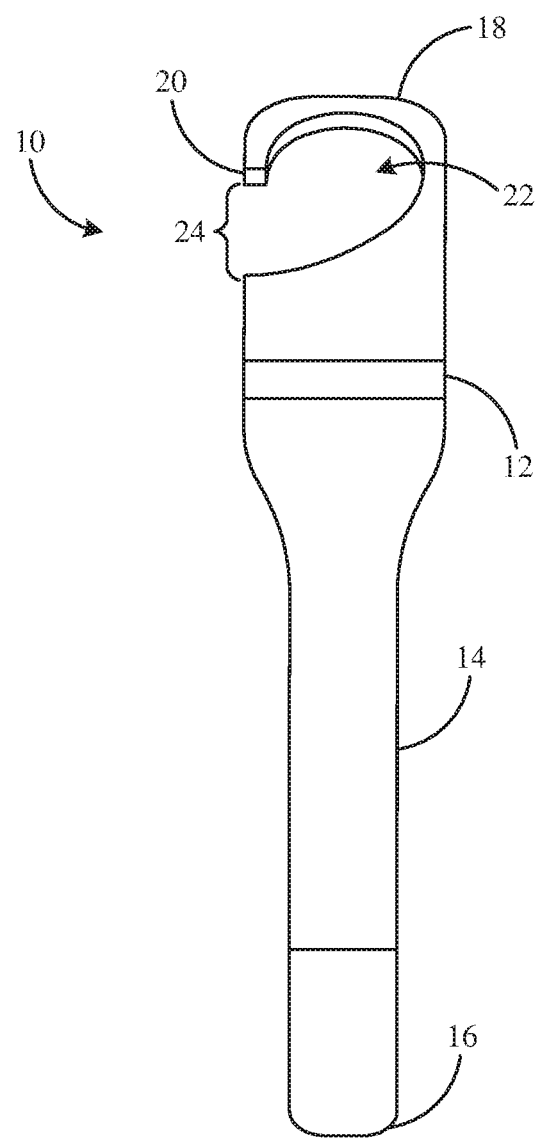
FIG. 2 is a top plan view of a first preferred embodiment of the retro-fitted external stabilizer bar of the present invention.

Reference is made first to FIG. 1 for a perspective view of a first preferred embodiment of the retro-fitted external stabilizer bar of the present invention. As shown in FIG. 1, stabilizer bar 10 includes bar handle 14, bar tip 16, and a wider shoulder area 12. The neck or hook portion 18 of bar 10 has hook tip 20 and forms C-shaped aperture 22. Hook portion 18 has inlet or opening 24 just wide enough to fit around the valve neck of the BVM resuscitator. Stabilizer bar 10 is preferably made from a rigid plastic, capable of withstanding sustained downward force. Other rigid yet resilient materials known to those skilled in the art may also be used to construct the stabilizer bar. Neck or hook portion 18 has sufficient tensile strength and flexibility to fit around the valve neck snugly and remain in position under pressure without cracking As also shown in FIG. 2, wider shoulder area 12 is of sufficient width to receive the primary impact of the downward force and transmit the sustained pressure to the valve connector of the BVM resuscitator.

Figure 3:
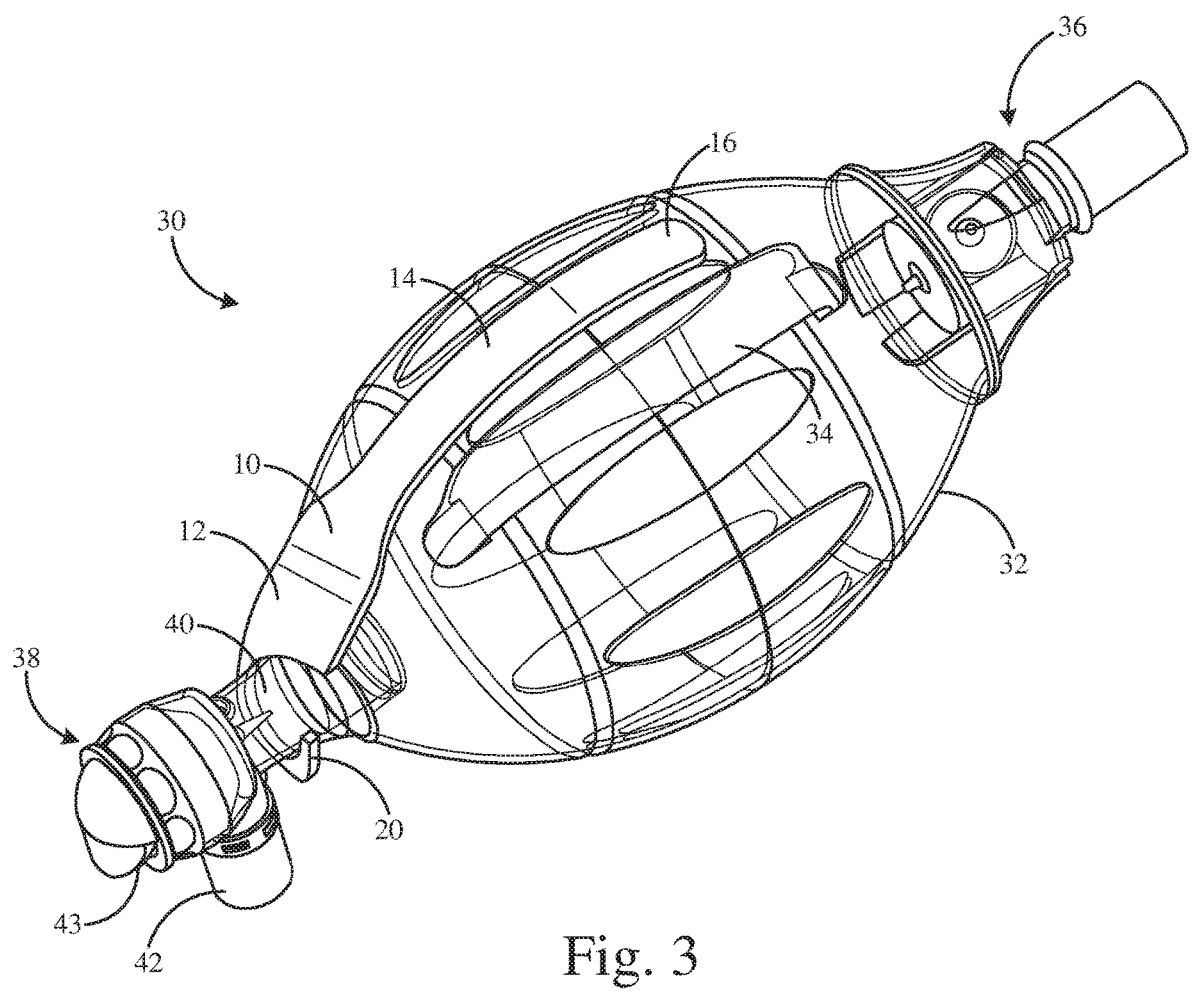
FIG. 3 is a perspective view of a first preferred embodiment of the retro-fitted external stabilizer bar of the present invention attached to the BVM resuscitator.

FIG. 3 provides a perspective view of the retro-fitted external stabilizer bar 10 of the present invention attached to the BVM resuscitator 30. The BVM resuscitator 30 has an inlet valve 36 through which air is delivered to the bag 32. Although some reservoir bags do not have a handle, bag 32 has handle 34 that serves as a positioning guide for the hand of the user. At the opposite end of bag 32 is connector 40 that joins bag 32 to outlet valve 38. Exit port 43 provides a release port for the release of exhaled air from the patient. Positioned on the side of outlet valve 38 is outlet port 42 through which pressurized air is delivered to the patient. As shown in FIG. 3, stabilizer bar 10 provides a rigid surface on the exterior of bag 32 for the user to exert downward pressure on connector 40 and outlet valve 38. The stabilizer bar may be lengthened or shortened in various alternate embodiments including but not limited to folding, telescoping, sliding, or snapping. This would allow the device to be extended to fit reservoir bags of varying size and to be stored in a compact space when not in use.

Figure 4:
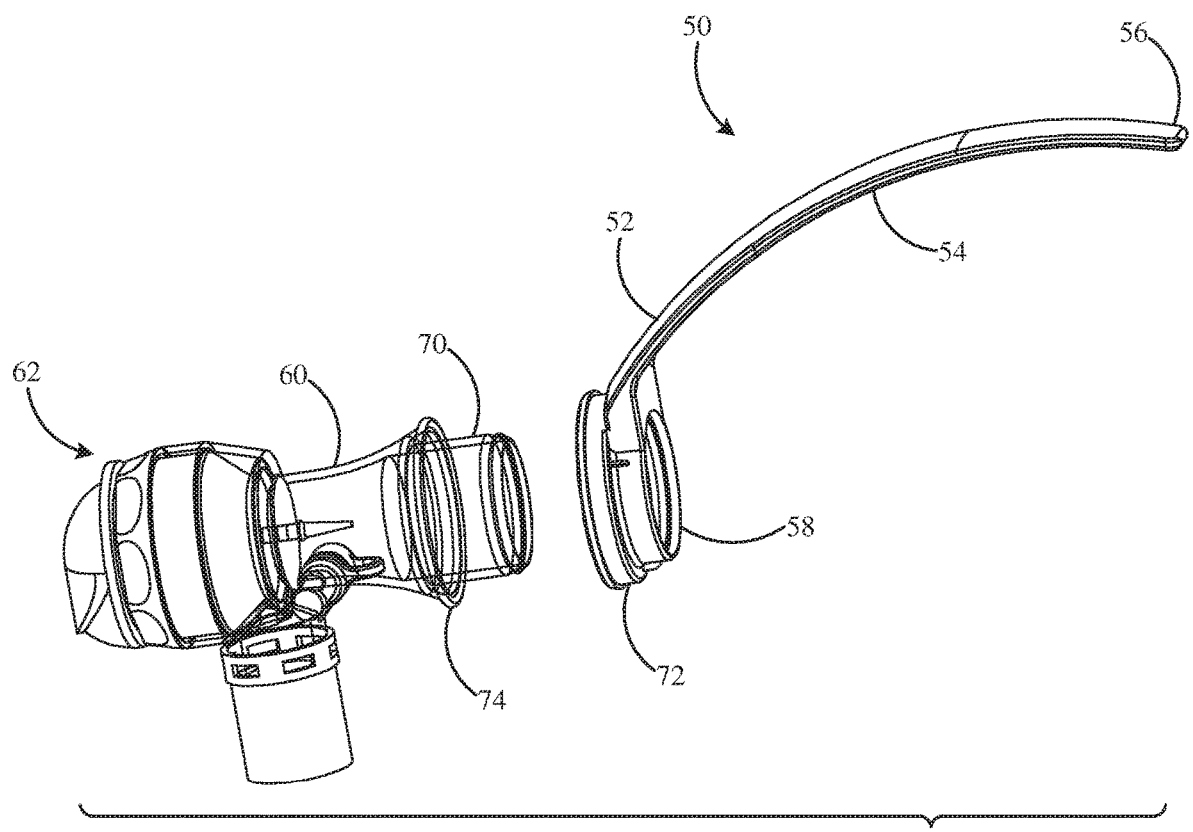
FIG. 4 is an exploded assembly view of an alternate preferred embodiment of the internal stabilizer bar and valve connector of the present invention.

Reference is next made to FIG. 4 which shows an exploded assembly view of an alternate preferred embodiment of the internal stabilizer bar 50 and valve connector 60 of the present invention. FIG. 4 shows the body 52 of the stabilizer bar 50 with curved handle 54 and end tip 56. Body 52 is attached to stabilizer ring 58 and ring connector seat 72 of stabilizer bar 50. As also shown in FIG. 4, valve connector 60 has connector tube 70 which fits inside stabilizer ring 58 and seals against valve connector seat 74. This connection may be a snap connection as shown in FIG. 4. Various other ways of connection are anticipated, which include but are not limited to a twist and lock connection, screw connection, or any other method which provides a secure, rigid connection of the stabilizer bar 50 to the connector tube 70. A detailed description of various alternate means of attachment is provided below with reference to FIGS. 13-15.

Figure 5A:
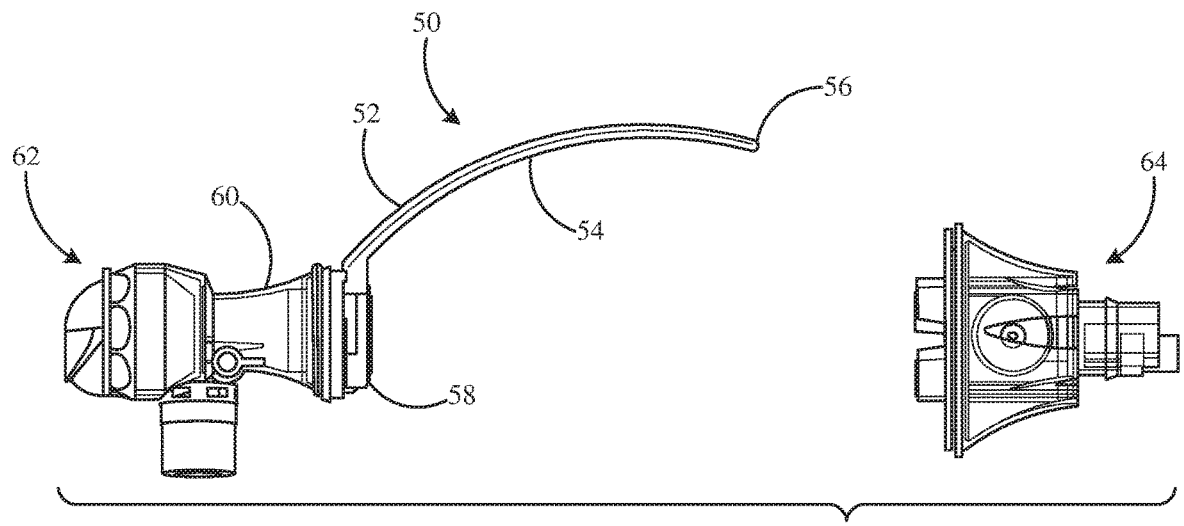
FIG. 5A is a partial assembly view of an alternate preferred embodiment of the internal stabilizer bar valve connector assembly and inlet valve of the present invention.
Figure 5B:
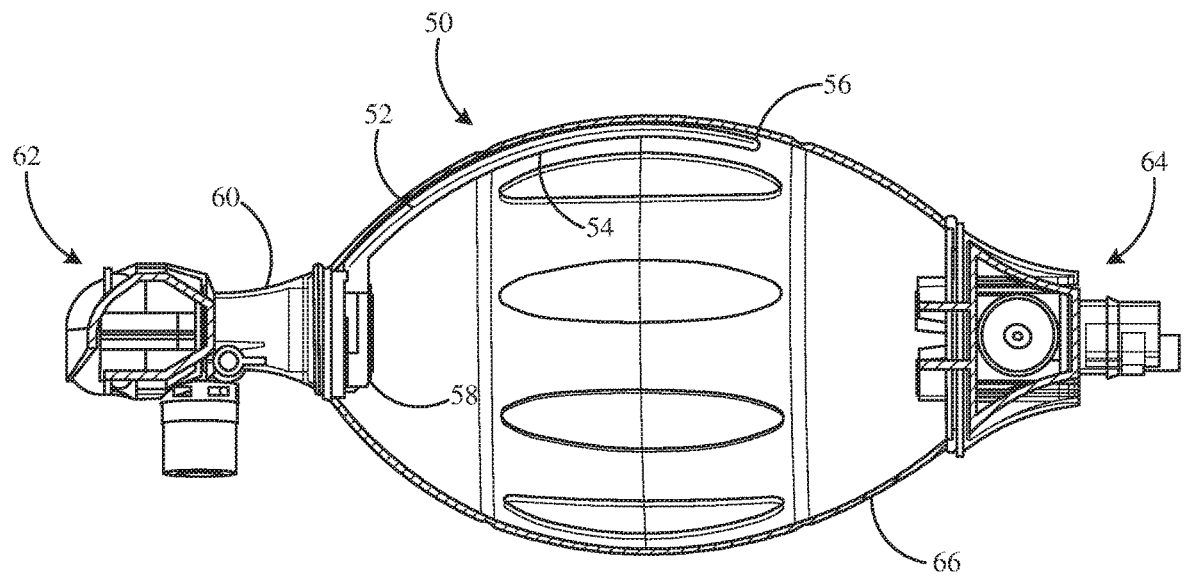
FIG. 5B is a cross-sectional view of an alternate preferred embodiment of the internal stabilizer bar of the present invention positioned within the bag valve assembly.
Figure 6A:
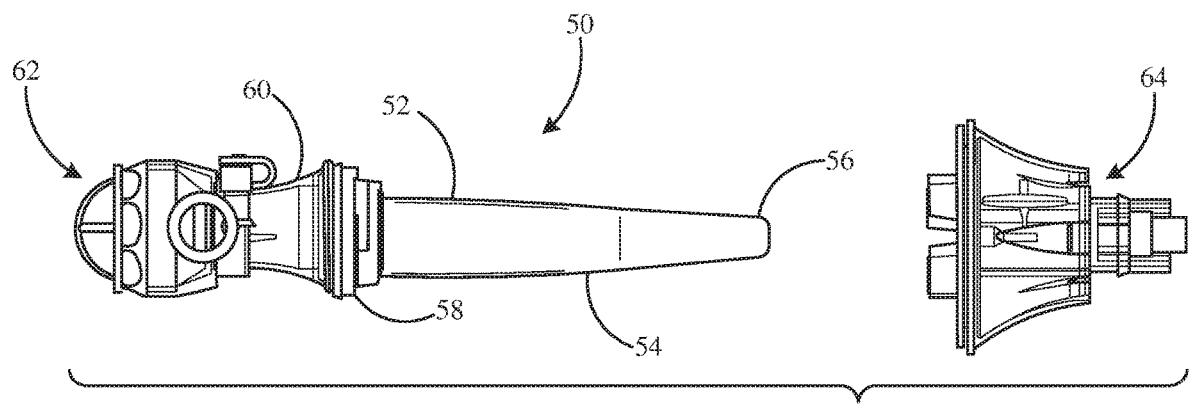
FIG. 6A is a bottom partial assembly view of an alternate preferred embodiment of the internal stabilizer bar valve connector assembly and inlet valve of the present invention.
Figure 6B:
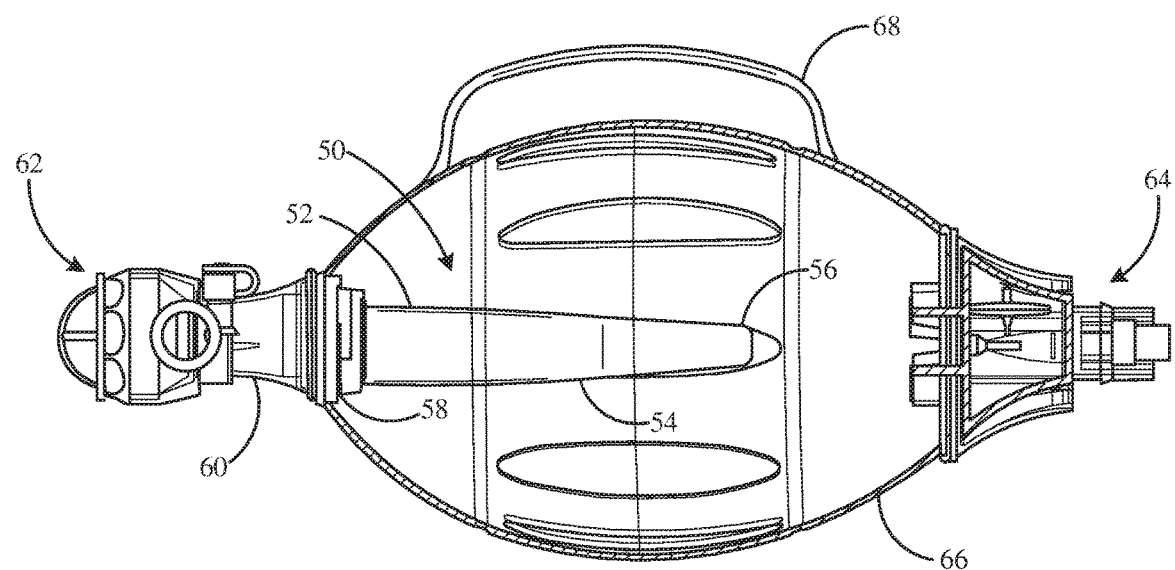
FIG. 6B is a bottom partial cross-sectional view of an alternate preferred embodiment of the internal stabilizer bar of the present invention positioned within the bag valve assembly.

As further disclosed in FIG. 4, valve connector 60 is attached to mask valve assembly 62. FIG. 5A also illustrates the internal stabilizer bar valve connector assembly (stabilizer bar 50 connected to valve connector 60) and inlet valve 64 of the present invention. Next, FIG. 5B illustrates a cross-sectional view of the bag valve assembly with the internal stabilizer bar 50 positioned within bag 66. FIG. 6A shows a bottom view of the internal stabilizer bar 50 connected to the valve connector assembly. The position of the internal stabilizer bar 50 within the bag valve assembly is shown in relation to bag 66, valve connector 60, and handle 68 in the bottom partial cross-sectional view of FIG. 6B.

Figure 7:
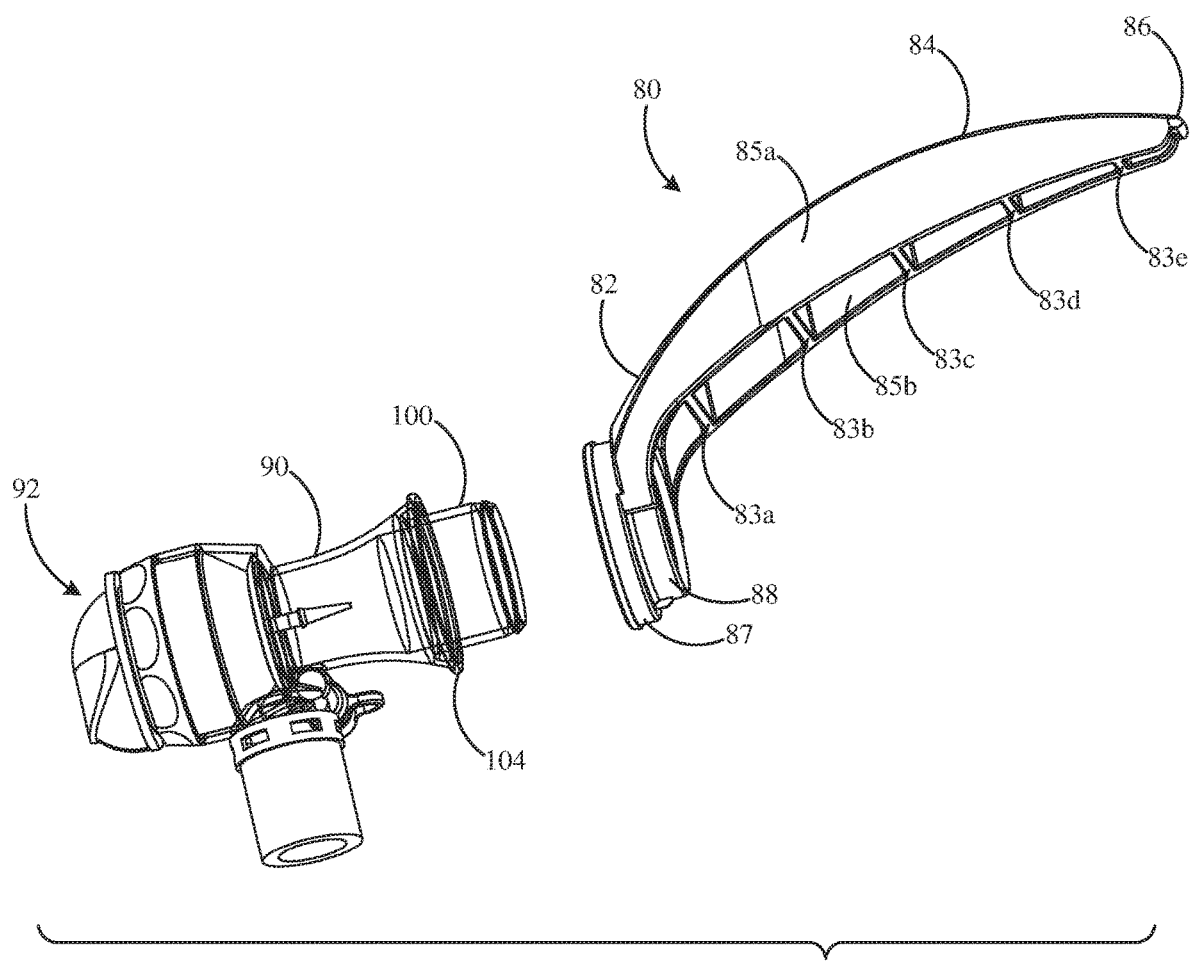
FIG. 7 is an exploded assembly view of an alternate preferred embodiment of the internal stabilizer bar and valve connector of the present invention.
Figure 8A:
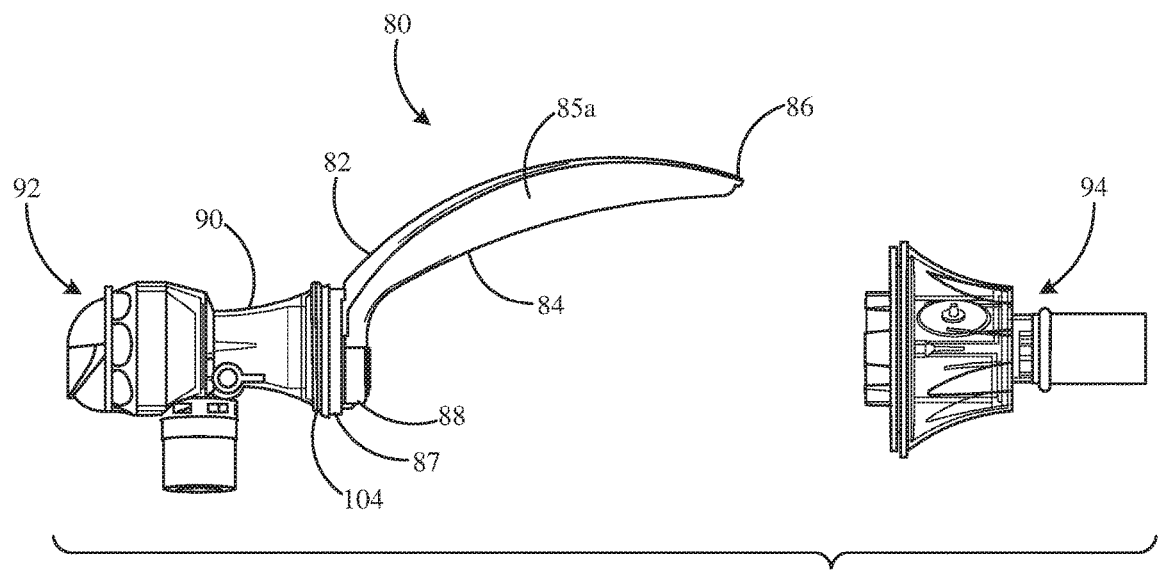
FIG. 8A is a partial assembly view of an alternate preferred embodiment of the internal stabilizer bar valve connector assembly and inlet valve of the present invention.
Figure 8B:
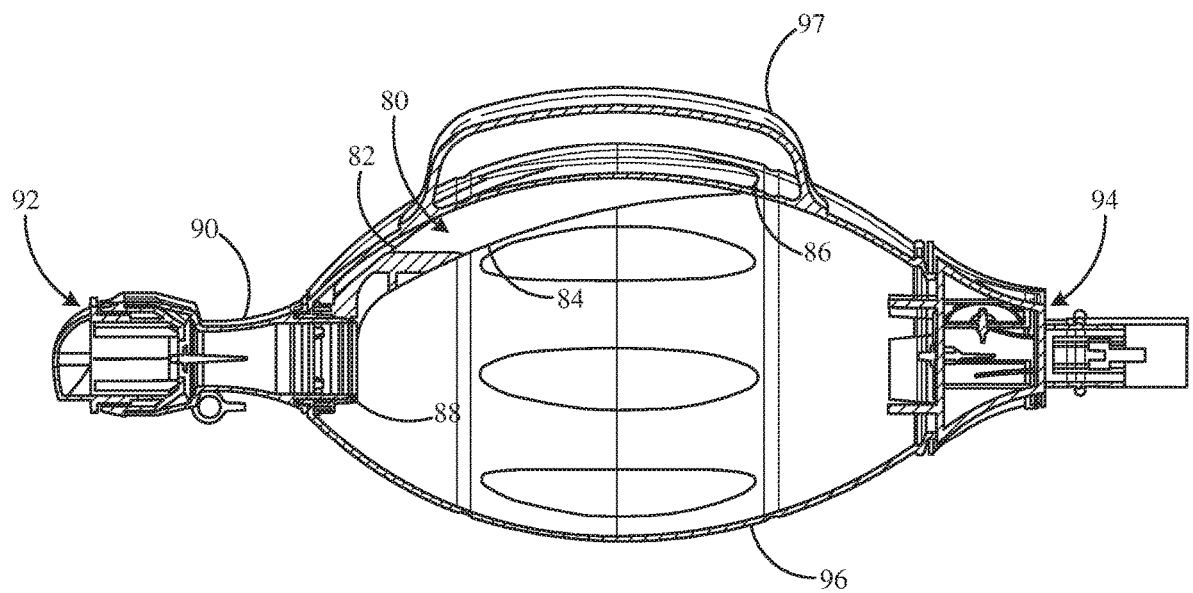
FIG. 8B is a side cross-sectional view of an alternate preferred embodiment of the internal stabilizer bar of the present invention positioned within the bag valve assembly.
Figure 9:
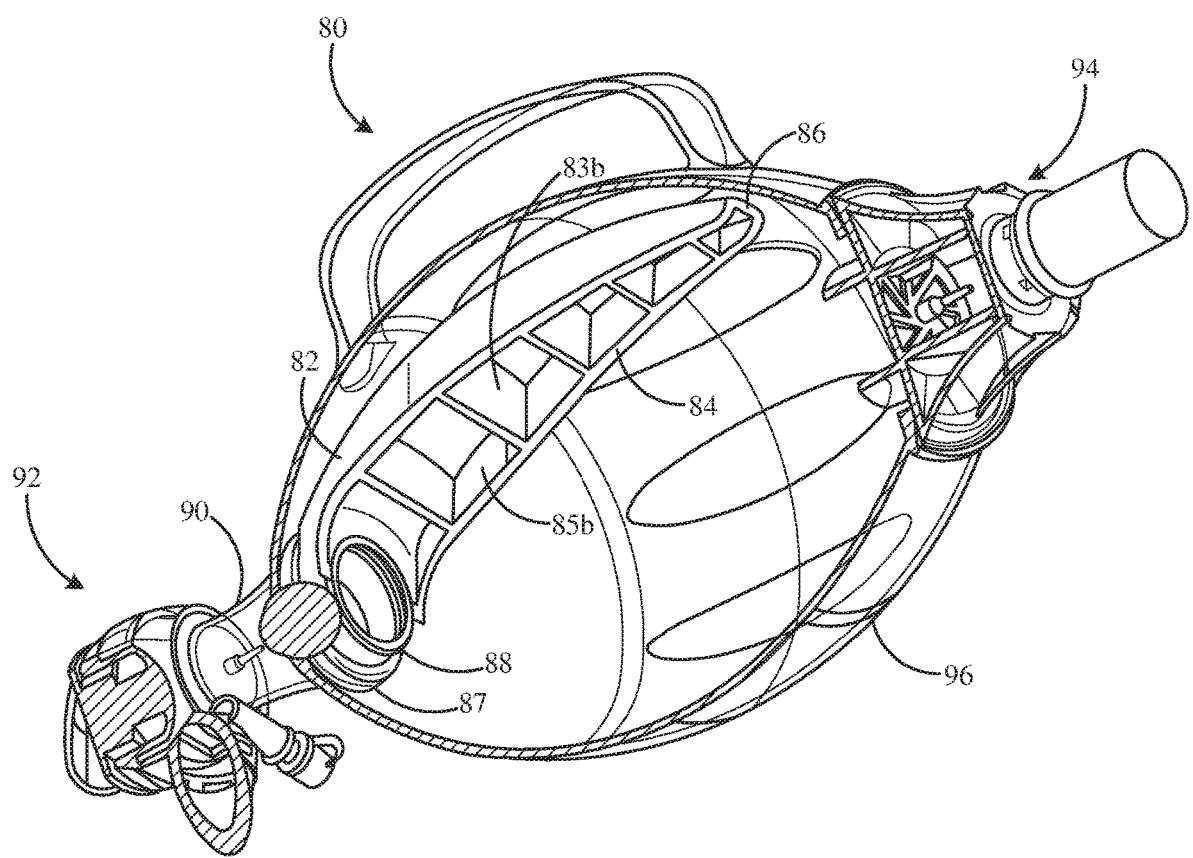
FIG. 9 is a perspective cross-sectional view of an alternate preferred embodiment of the internal stabilizer bar of the present invention positioned within the bag valve assembly.

Continuing in FIGS. 7-9, is another alternate preferred embodiment of the internal stabilizer bar and valve connector of the present invention. FIG. 7 illustrates an exploded assembly view of the stabilizer bar 80 along with valve connector 90. FIG. 7 shows the body 82 of stabilizer bar 80, having curved handle 84 and end tip 86. In this embodiment, body 82 has proximal side wall 85a and distal side wall 85b. Within body 82 between side walls 85a and 85b, are a plurality of structural cross walls shown as 83a, 83b, 83c, 83d, and 83e. These cross walls provide increased strength and rigidity to the body 82 of stabilizer bar 80. The stabilizer bar may be lengthened or shortened in various alternate embodiments including but not limited to folding, telescoping, sliding, or snapping. This would allow the device to be extended to fit reservoir bags of varying size and to be stored in a compact space when not in use.

Body 82 is attached to stabilizer ring 88 and ring connector seat 87 of stabilizer bar 80. As also shown in FIG. 7, valve connector 90 has connector tube 100 which fits inside stabilizer ring 88 and seals against valve connector seat 104. This connection may be a snap connection, twist and lock connection, screw connection, or any other method which provides a secure, rigid connection of the stabilizer bar 80 to the connector tube 100. Additional detail regarding further alternate embodiments for making this connection are described in greater detail below with reference to FIGS. 13-15. FIG. 7 also shows valve connector 90 attached to mask valve assembly 92.

FIG. 8A also illustrates the internal stabilizer bar valve connector assembly (stabilizer bar 80 connected to valve connector 90) and inlet valve 94 of the present invention. Next, FIG. 8B illustrates a cross-sectional view of the bag valve assembly with the internal stabilizer bar 80 positioned within bag 96 having handle 97. FIG. 9 shows a perspective cross-sectional view of the internal stabilizer bar 80 positioned within the bag valve assembly. The position of the internal stabilizer bar 80 within the bag valve assembly is shown in relation to bag 96, valve connector 90, and inlet valve 94. FIG. 9 also illustrates structural cross wall 83b positioned against distal side wall 85b of the stabilizer body 82.

Figure 16:
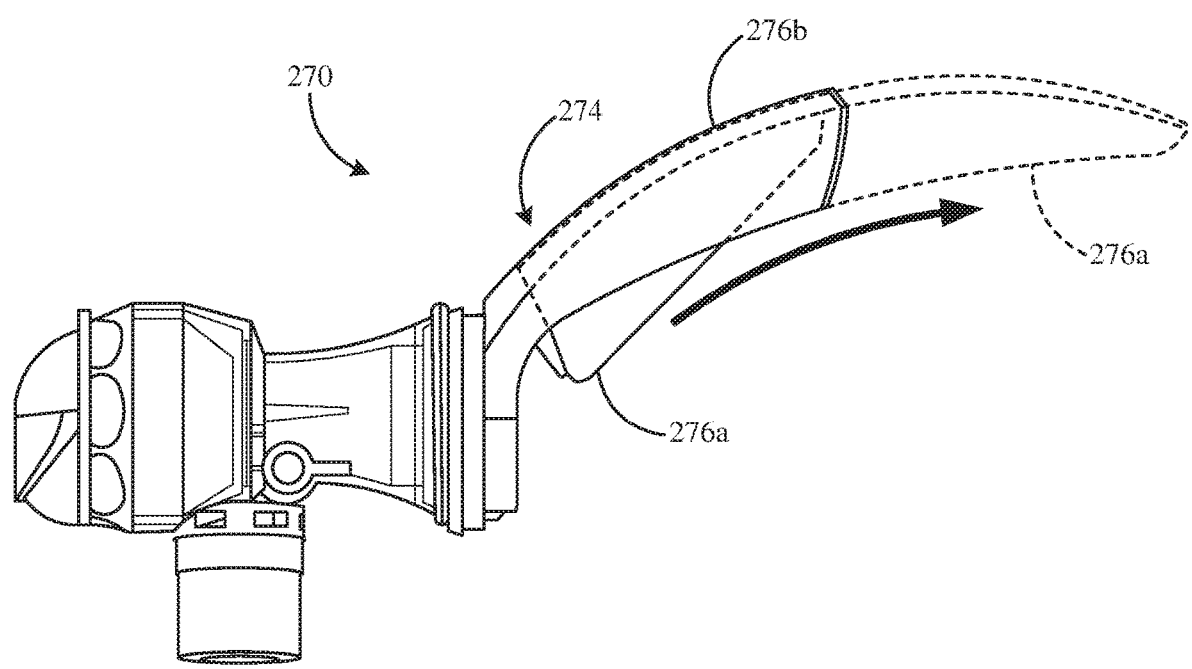
FIG. 16 is a perspective view of an alternate embodiment of the stabilizer bar of the present invention.

FIG. 16 illustrates a perspective view of the stabilizer bar 270 showing the extension arm member 274 of the stabilizer bar comprised of two elements. In this embodiment, as shown in FIG. 16, the first element 276a is movable with respect to the second element 276b, such that the extension arm member 274 may be extended for use and collapsed for storage. In various alternate embodiments, it is envisioned that the extension arm member may be comprised of more than two elements. In this manner, the stabilizer bar may be lengthened or shortened by various methods including but not limited to folding, telescoping, sliding, or snapping. This would allow the device to be extended to fit reservoir bags of varying size and to be stored in a compact space when not in use.

Figure 10A:
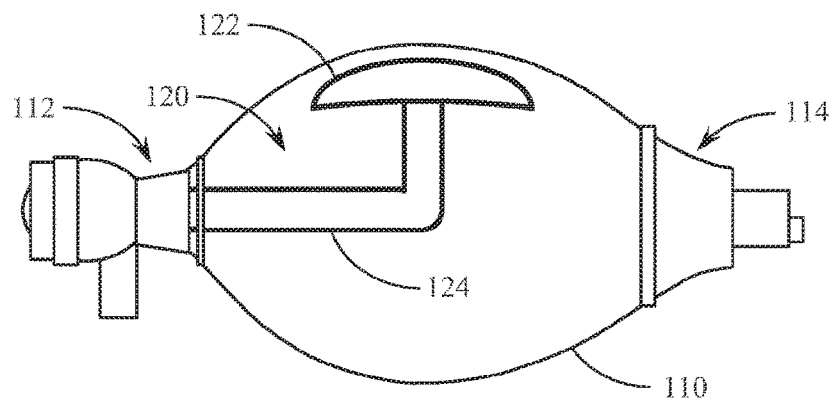
FIG. 10A is a schematic partial cross-sectional view of an alternate embodiment of the internal stabilizer bar of the present invention positioned within the bag valve assembly.

Continuing with FIGS. 10A, 10B, 10C, and 10D, are four alternate embodiments of the internal stabilizer bar of the present invention positioned within the bag valve assembly. FIG. 10A illustrates the basic components of the bag valve assembly: the reservoir bag 110, outlet valve assembly 112, and the inlet valve assembly 114. Additionally, FIG. 10A shows stabilizer arm 120 having the body 124 of the support arm extending from the neck of the outlet valve assembly toward the center of the bag and angle upward. The top of the arm is connected to a support lever 122. The support lever is configured to receive the downward force from the user. In alternate embodiments, the support lever in FIGS. 10A, 10B, 10C, and 10D may be configured to lengthen or shorten in various ways including but not limited to folding, telescoping, sliding, or snapping means from a shortened to an extended length. This would allow the device to be extended to fit reservoir bags of varying size and to be stored in a compact space when not in use.

Figure 10B:
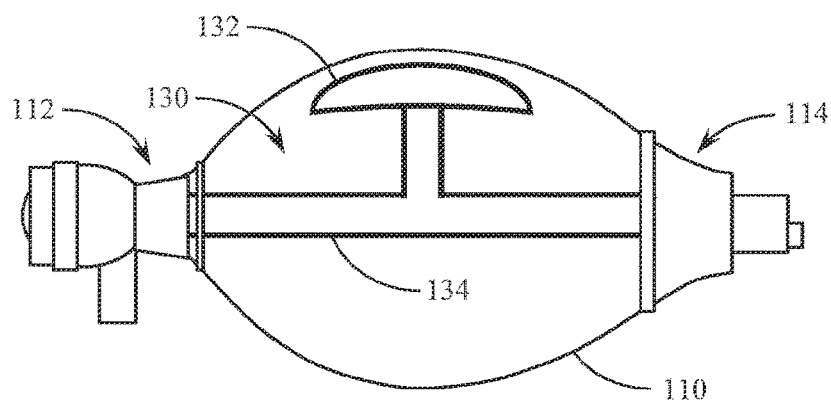
FIG. 10B is a schematic partial cross-sectional view of an alternate embodiment of the internal stabilizer bar of the present invention positioned within the bag valve assembly.

FIG. 10B illustrates the same basic components of the bag valve assembly. In this embodiment, however, stabilizer arm 130 has body 134 spanning the length of the reservoir bag 110 with an extension rising from the body toward the top of the bag. In this embodiment, the top of the extension is connected to a support lever 132 which receives the downward force from the user.

Figure 10C:
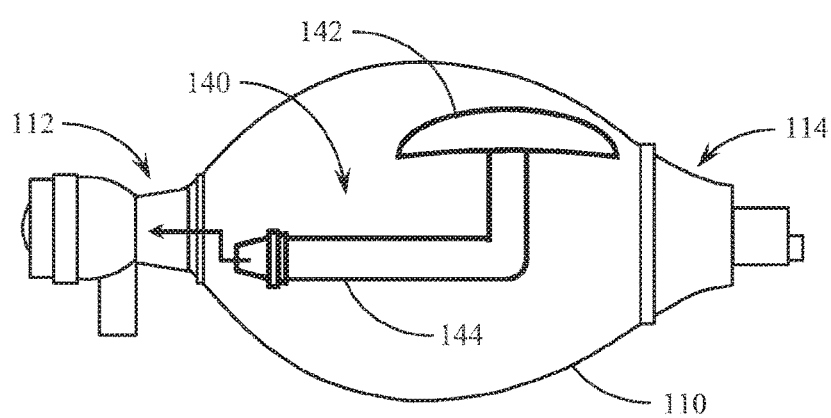
FIG. 10C is a schematic partial cross-sectional view of an alternate embodiment of the internal stabilizer bar of the present invention positioned within the bag valve assembly.

FIG. 10C illustrates one of the many possible ways that the stabilizer bar 140 may be attached to the outlet valve assembly 112. While the primary requirements are that the attachment be secure and rigid, many methods of attachment well known in the art will accomplish the functional requirements for this connection. The connection can be a snapping connection as shown in FIG. 10C, or it can be any of a number of other options including but not limited to twist and lock or screw assembly attachment. The connection must be secure such that the stabilizer arm does not come loose during use. Such a fixed attachment ensures that the stabilizer bar 140 functions properly. For the original equipment manufactured stabilizer bar, the construction of the outlet valve assembly and stabilizer bar can be formed as a single unit, or can be constructed of multiple pieces that form the stabilizer bar and hold the bag in place. The stabilizer bar can also be integrated into the bag.

Figure 10D:
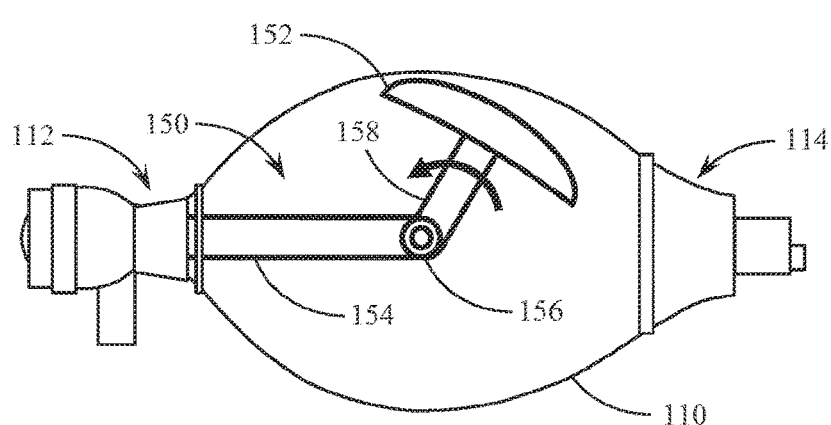
FIG. 10D is a schematic partial cross-sectional view of an alternate embodiment of the internal stabilizer bar of the present invention positioned within the bag valve assembly.

FIG. 10D illustrates the internal stabilizer bar 150 positioned within the bag valve assembly. In this embodiment, stabilizer bar 150 articulates around hinge 156. The stabilizer bar 150 is composed of four parts: connector arm 154, hinge 156, upright arm 158, and support lever 152. In this embodiment, the stabilizer bar 150 articulates for easier placement and assembly.

Figure 11A:
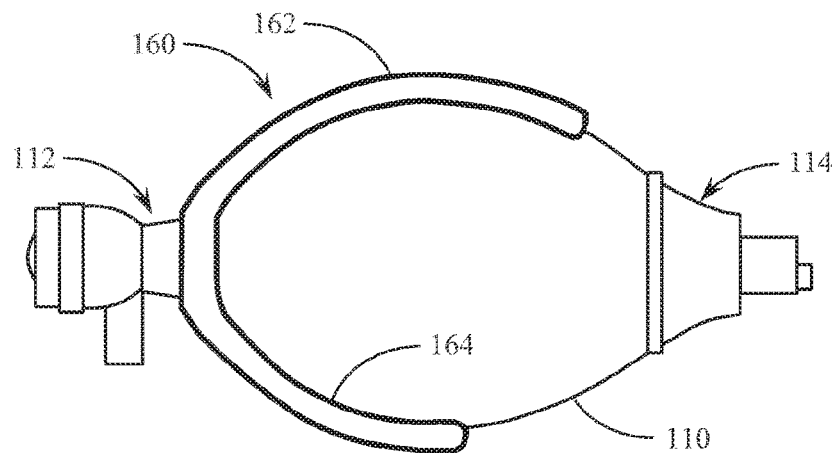
FIG. 11A is a side view of an alternate embodiment of the external stabilizer bar of the present invention.
Figure 11B:
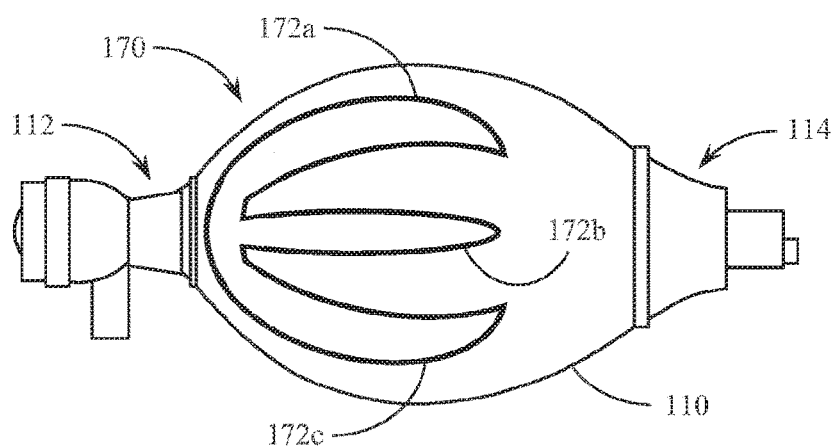
FIG. 11B is a side view of an alternate embodiment of the stabilizer bar of the present invention.
Figure 11C:
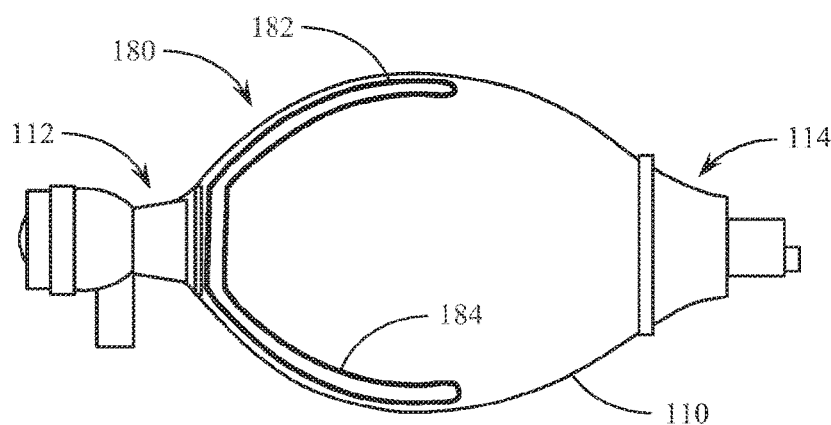
FIG. 11C is a partial cross-sectional view of an alternate embodiment of the internal stabilizer bar of the present invention.

FIG. 11A illustrates an alternate embodiment of the external stabilizer bar of the present invention. As shown in FIG. 11A, stabilizer bar 160 has arm 162 on top of the reservoir bag 110 and arm 164 on the bottom of the reservoir bag. Such a configuration adds additional structural support and rigidity to the connection between the bag 110 and the outlet valve connector 112. Stabilizer bar 160 can be molded into outlet valve connector 112. FIG. 11C shows a similar configuration with an internal stabilizer bar of the present invention. Here, stabilizer bar 180 is positioned inside reservoir bag 110 with arm 182 extending to the top of the bag and arm 184 extending to the bottom of the bag. Again, such a configuration is designed to increase the rigidity and support at the connection between the bag and the outlet valve assembly. Finally, the alternate embodiment of FIG. 11B illustrates the use of a stabilizer bar 170 having a plurality of arms 172a, 172b, and 172c. This configuration may be positioned internal or external to the reservoir bag 110 or built into the material of the bag itself, and would also increase support at the connection between the bag and the outlet valve assembly.

Figure 12A:
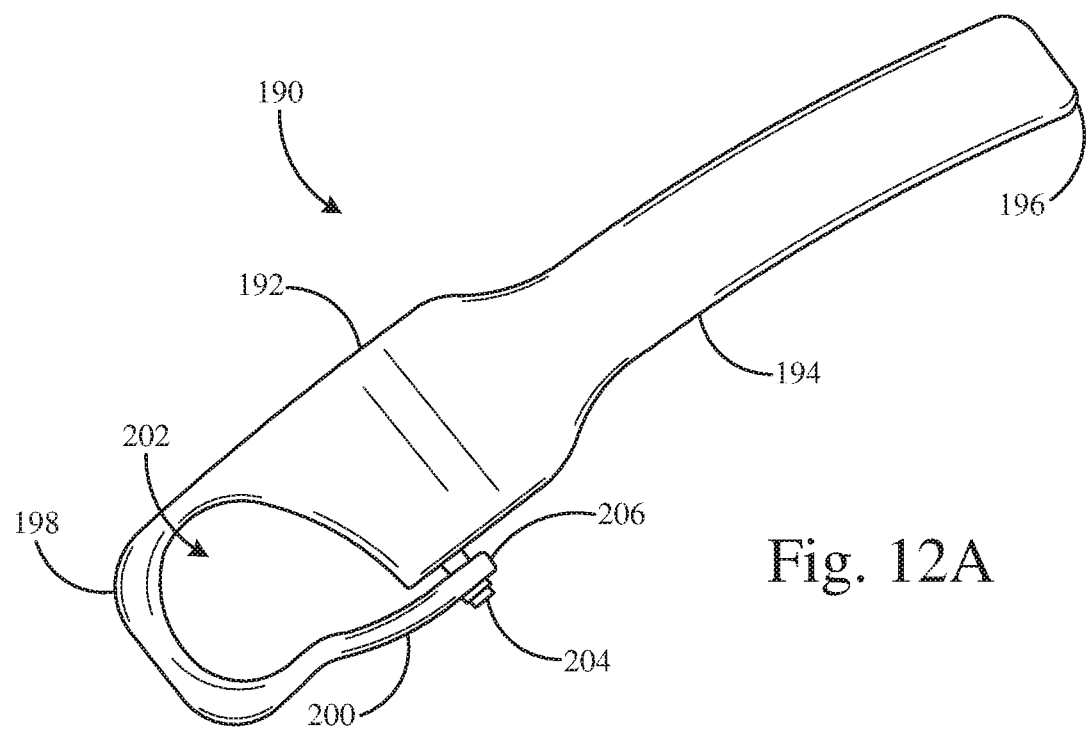
FIG. 12A is a perspective view of an alternate embodiment of the retro-fitted external stabilizer bar of the present invention.

FIG. 12A is a perspective view of an alternate embodiment of the retro-fitted external stabilizer bar 190 of the present invention. In FIG. 12A, stabilizer bar 190 has the body 194, tip 196, and shoulders 192 of the primary embodiment, but also has a snap closure structure at the end of hook 198. Aperture 202 is formed from hook 198 and closure arm 200. Closure arm 200 has snap ring 206 which is configured to fit around snap post 204. In this embodiment, the stabilizer bar 190 is securely attached to the neck of the outlet valve connector. It is envisioned, of course, that any connective device known in the art to fasten, clip, connect, or secure two members for support could be utilized in place of the snap closure.

Figure 12B:
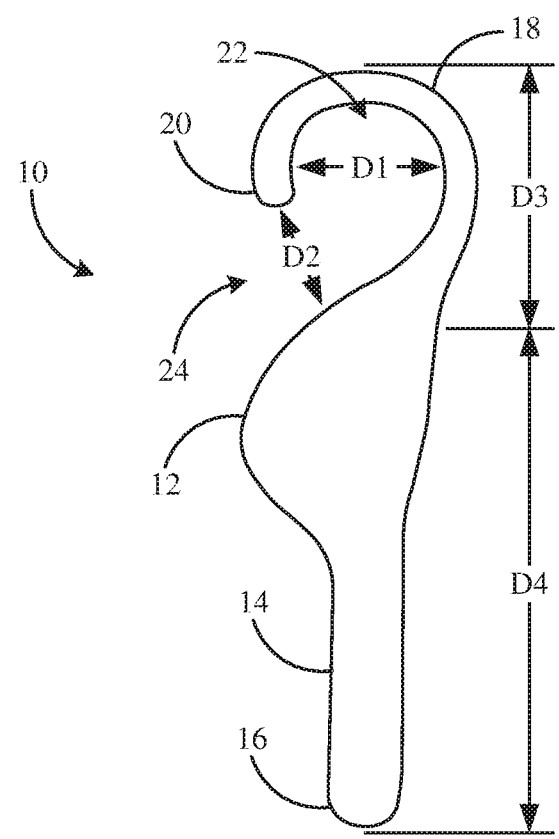
FIG. 12B is a schematic diagram of a generic embodiment of the retro-fitted external stabilizer bar of the present invention.

FIG. 12B is a schematic diagram of a generic embodiment of the retro-fitted external stabilizer bar of the present invention. In FIG. 12B, stabilizer bar 10 is shown having tip 16, handle 14, body 12, hook 18, end of hook 20. As previously described, the stabilizer bar 10 has a handle portion 14 that extends over the reservoir bag and acts as the resting point for the bagging hand. The handle 14 of the stabilizer bar 10 would be wide enough to provide ample support but narrow enough to allow a bagging hand of various sizes (due to anatomical differences in providers) to press downward, but also allow the user to completely squeeze the bag. The preferred embodiment stabilizer bar would have a handle 14 which is ½ inch wide, and which extends over the bag (D3 and D4) 5 to 7 inches from the outlet valve connection. In alternate embodiments, the shape, width, length, and thickness of the stabilizer bar may vary. The thickness and dimensions of the various parts of the stabilizer bar 10 are configured to optimally fit the size of the reservoir bag and outlet valve connector (adult, child, infant, etc.). While thickness of the stabilizer bar could vary, the preferred embodiment would have a thickness of ⅛ inch. The stabilizer bar would have a shape or curvature compatible with the BVM resuscitators currently in use so as to allow the stabilizer bar to rest close to or on the outer surface of the bag portion of the BVM resuscitator.

As described above, the stabilizer bar has a neck region or hook that is positioned around the hard plastic valve connector of the BVM resuscitator. While dimensions could range widely, the minimum opening is wide enough to allow the valve connector of the BVM resuscitator to slip into the opening and remain in the opening throughout placement and use of the stabilizer bar. In the preferred embodiment, this distance D2 of opening 24 as shown in FIG. 12B is preferably 1⅛ inches. Aperture 22 allows the outlet valve connector of the BVM resuscitator to settle into position during placement of the stabilizer bar. As the stabilizer bar is pulled toward the bag (pulled away from the valve region and secured into place) so as to allow the bagging hand to rest on it in the appropriate region of the bag (the portion that allows the user to squeeze the bag appropriately) the valve region of the BVM resuscitator is forced into aperture 22. While dimensions may vary, in the preferred embodiment distance D1 of aperture 22 is preferably 1⅛ inches.

Figure 13:
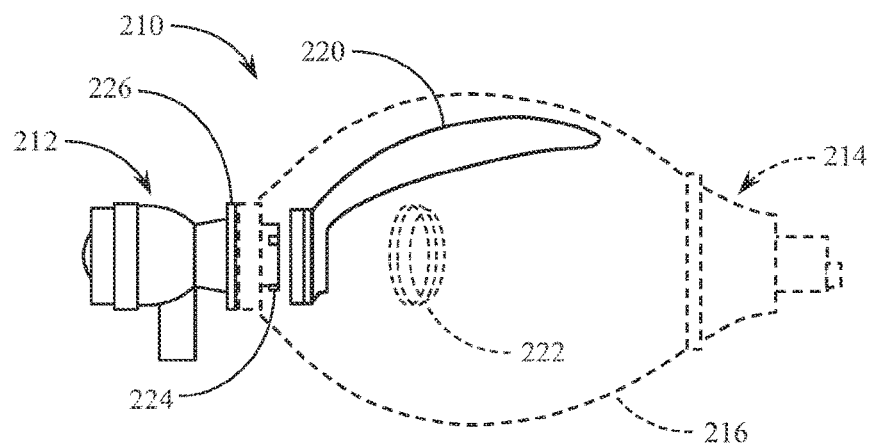
FIG. 13 is a schematic assembly side view of an alternate preferred embodiment of the internal stabilizer bar of the present invention positioned within the multi piece construction bag valve assembly.

FIG. 13 is a schematic assembly side view of an alternate preferred embodiment of the internal stabilizer bar of the present invention positioned within the multi piece construction bag valve assembly. Some current BVM resuscitator assemblies utilize multi piece construction, having an outlet valve assembly and an attachment ring. The attachment ring secures the reservoir bag to the outlet valve assembly. In this retro-fitted configuration, as shown in FIG. 13, the ring 222 may be removed from the outlet valve assembly 212 and replaced with stabilizer bar 220. The stabilizer bar 220 connects to the attachment mechanism 224 on the connector tube. The reservoir bag 216 is held in place between the base of the stabilizer bar 220 and the valve connector seat 226.

Figure 14:
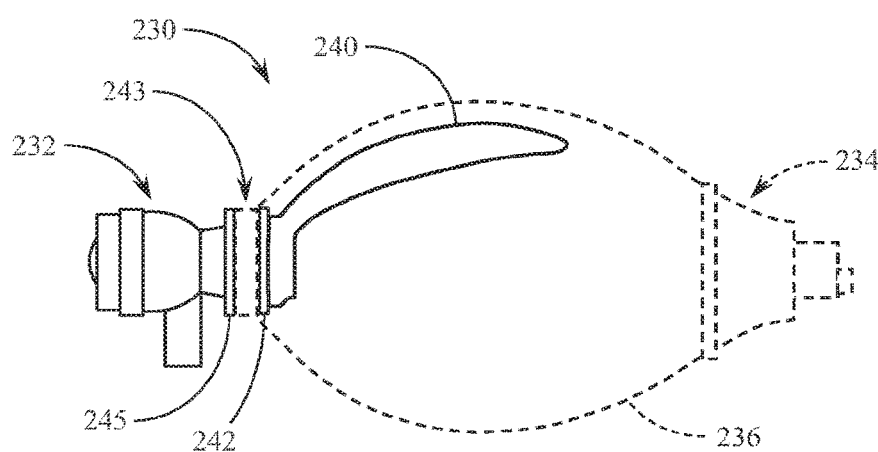
FIG. 14 is a schematic assembly side view of an alternate preferred embodiment of the original equipment manufactured internal stabilizer bar of the present invention positioned within the one piece construction bag valve assembly.

FIG. 14 is a schematic assembly side view of an alternate preferred embodiment of the original equipment manufactured internal stabilizer bar of the present invention positioned within the one piece construction bag valve assembly.

Some current BVM resuscitator assemblies utilize single piece construction, having an outlet valve assembly with a channel for receiving the neck of the reservoir bag. The neck of the reservoir bag is stretched over the mouth of the outlet valve assembly and held in place within a channel where the bag rests on the outlet valve connector. As shown in FIG. 14, in alternate preferred embodiment 230, the stabilizer bar 240 and the outlet valve assembly 232 are molded as a single piece during original manufacture. Alternately, the stabilizer bar may be attached and affixed to the outlet valve assembly by a variety of means including but not limited to adhesive, cement, or sonic welding. During assembly, the reservoir bag 236 is slipped over both the stabilizer bar 240 and the mouth 242 of the outlet valve assembly 232 and held in place within the channel 243 on the outlet valve connector 245.

Figure 15:
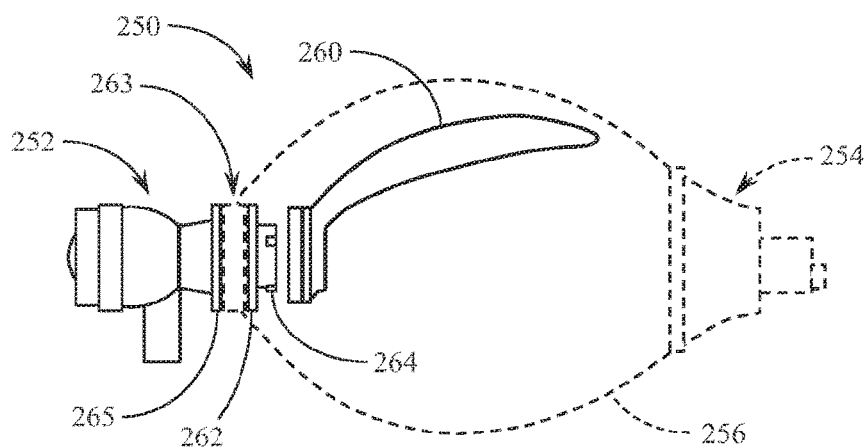
FIG. 15 is a schematic assembly side view of an alternate preferred embodiment of the original equipment manufactured internal stabilizer bar of the present invention positioned within the multi piece construction bag valve assembly.

FIG. 15 is a schematic assembly side view of an alternate preferred embodiment of the original equipment manufactured internal stabilizer bar of the present invention positioned within the two piece construction bag valve assembly. As discussed above, in a BVM resuscitator having a single piece construction outlet valve assembly, the neck of the reservoir bag is stretched over the mouth of the outlet valve assembly and held in place within the channel on the outlet valve connector. As shown in FIG. 15, in alternate preferred embodiment 250, the attachment mechanism 264 on the connector tube 265 is configured during original manufacture to securely attach to the stabilizer bar 260. Reservoir bag 256 is attached to mouth 262 of the outlet valve assembly 252 and held in place within the channel 263 on the outlet valve connector 265. During assembly, the stabilizer bar is connected to attachment mechanism 264.

Figure 17A:
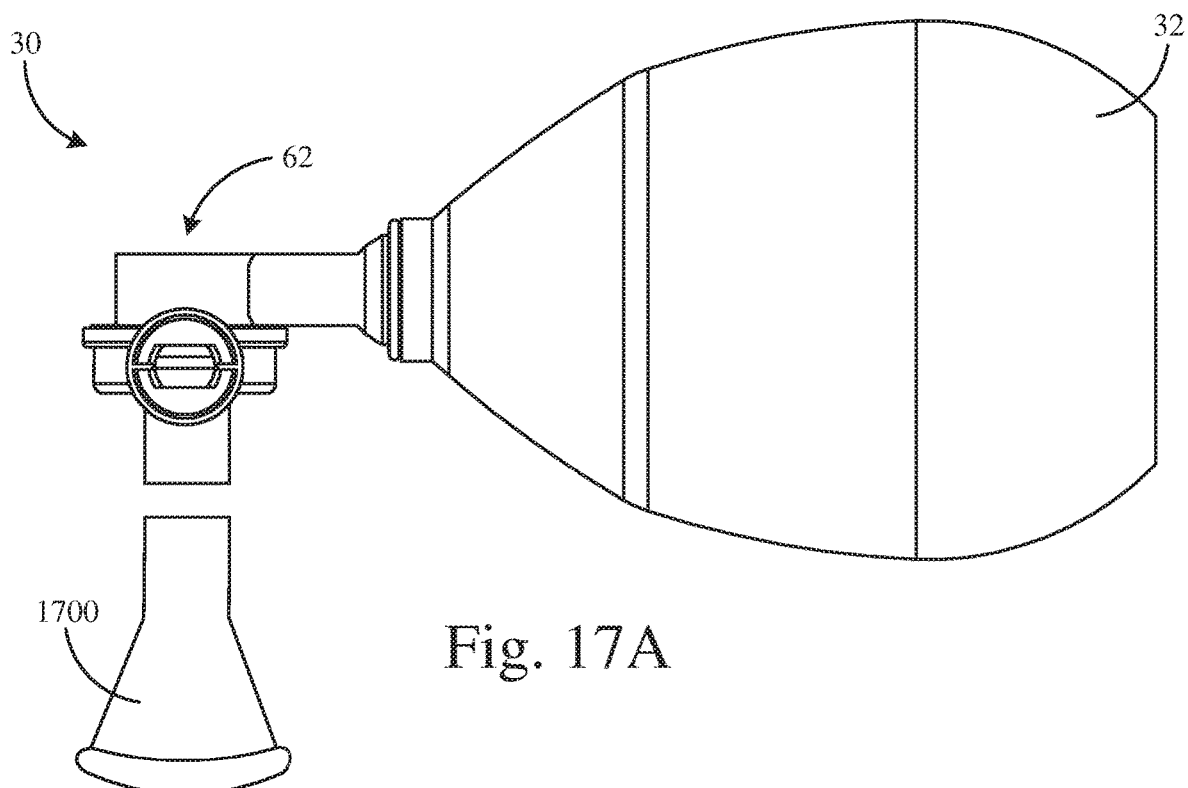
FIG. 17A is a side view of an embodiment of the BVM resuscitator according to an embodiment of the disclosure.
Figure 17B:
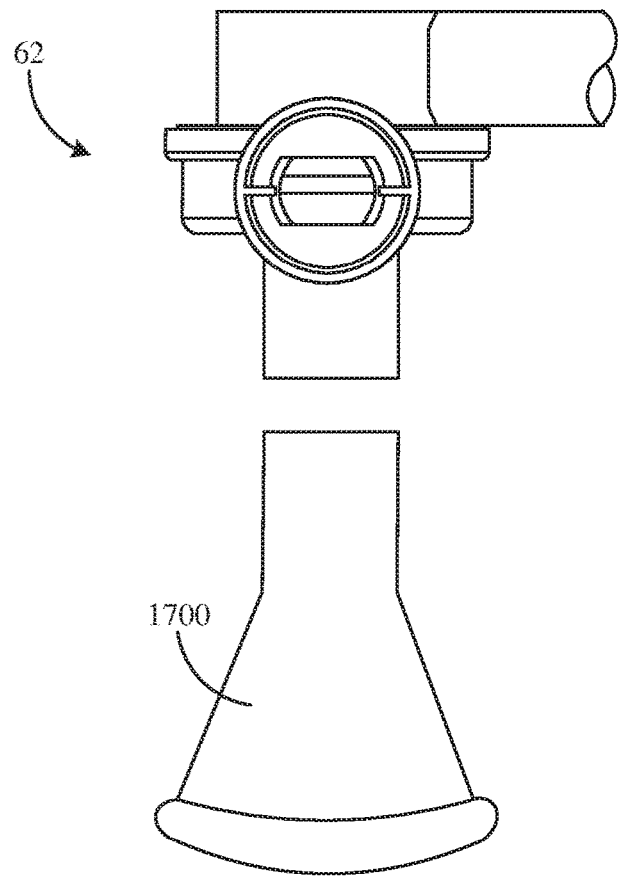
FIG. 17B is a side view of an embodiment of the mask valve assembly and face mask according to the embodiment of FIG. 17A.

FIGS. 17A-B are side views of an embodiment of a BVM resuscitator, mask valve assembly, and face mask according to an embodiment of the disclosure. In the embodiments shown, the BVM resuscitator 30 has a reservoir bag 32 coupled to mask valve assembly 62 as described previously. In the embodiments shown, face mask 1700 is coupled to mask valve assembly 62 and is configured to cover the nose and/or face of a patient.

Figure 18A:
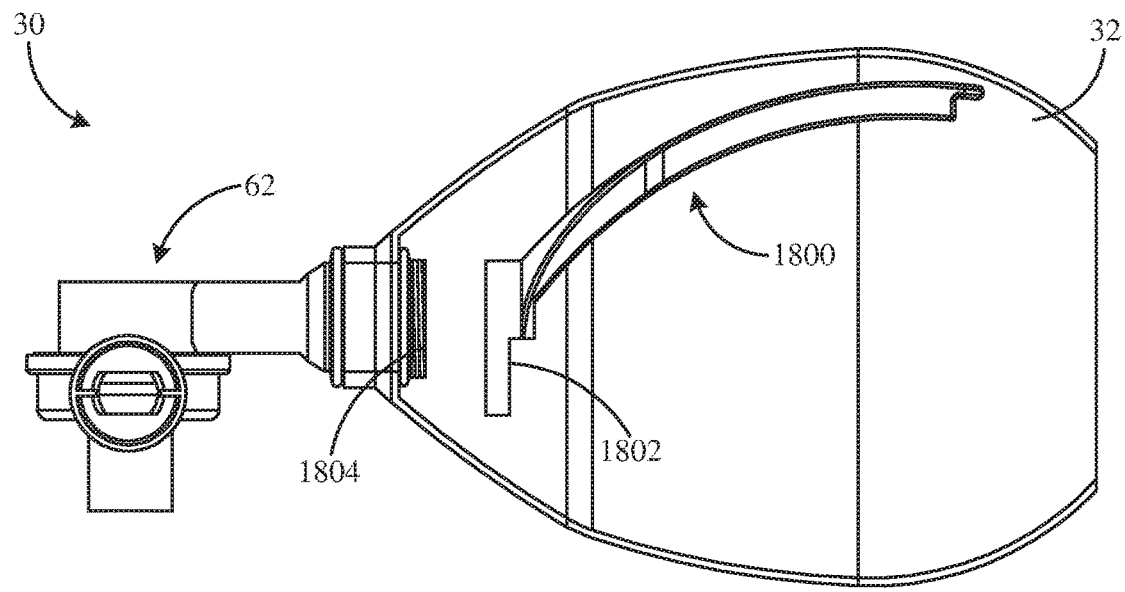
FIG. 18A is a side view of an embodiment of the BVM resuscitator according to an embodiment of the disclosure.
Figure 18B:
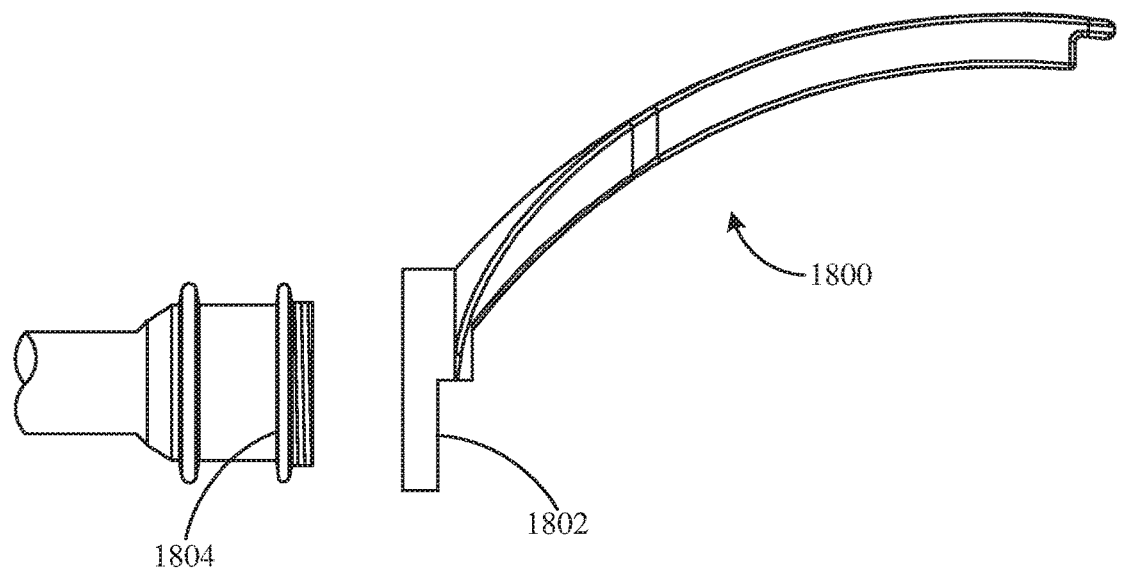
FIG. 18B is a side view of an embodiment of the stabilizer bar and connector according to the embodiment of FIG. 18A.

FIG. 18A-B are side views of an embodiment of the BVM resuscitator, mask valve assembly, stabilizer bar, and connector according to an embodiment of the disclosure. In the embodiments shown, the BVM resuscitator 30 has a reservoir bag 32 coupled to mask valve assembly 62 as previously discussed. In the embodiments shown, stabilizer bar 1800 has threads 1802 that couple to threads 1804 in a screw connection as described previously.

Changes in the precise embodiments of the invention herein disclosed can be made within the scope of what is claimed without departing from the spirit of the invention. Other designs may be evident to those skilled in the art upon viewing this device. Although the present invention has been described in conjunction with a number of preferred embodiments, those skilled in the art will recognize modifications to these embodiments that still fall within the spirit and scope of the present invention.

The invention claimed is:

1. A bag valve mask (BVM) resuscitator comprising:
    a collapsible reservoir bag having an inlet valve and an output opening;
    an outlet valve having a hard plastic rigid connector and an outlet port, wherein one end of the rigid connector is directly coupled to the output opening of the reservoir bag and the opposite end of the rigid connector is directly coupled to the outlet port;
    a face mask directly coupled to the outlet port; and
    a rigid stabilizer bar directly coupled to the rigid connector and extending along a length of the reservoir bag, wherein the rigid stabilizer bar is configured to prevent compression of the reservoir bag in a plane of the rigid stabilizer bar,
    wherein the reservoir bag is configured to be fully compressible in a plane other than the plane of the rigid stabilizer bar.

2. The BVM resuscitator of claim 1, wherein the rigid connector is configured as an anchoring point for one end of the rigid stabilizer bar and is configured to transfer downward pressure to the face mask when downward force is applied to the rigid stabilizer bar in the plane of the rigid stabilizer bar.

3. The BVM resuscitator of claim 2, wherein the one end of the rigid stabilizer bar is a fulcrum for the rigid stabilizer bar.

4. The BVM resuscitator of claim 2, wherein the rigid stabilizer bar comprises an open collar at the one end configured to couple to the rigid connector.

5. The BVM resuscitator of claim 2, wherein the rigid stabilizer bar comprises a closed collar at the one end configured to couple to the rigid connector.

6. The BVM resuscitator of claim 1, wherein the rigid stabilizer bar is removably connectable to the rigid connector.

7. The BVM resuscitator of claim 1, wherein the rigid stabilizer bar is positioned external to the reservoir bag, wherein leverage created during use is focused at the face mask.

8. The BVM resuscitator of claim 1, wherein the rigid stabilizer bar is positioned internal to the reservoir bag, wherein leverage created during use is focused at the face mask.

9. The BVM resuscitator of claim 1, wherein the stabilizer bar is integrated into a wall of the reservoir bag, wherein leverage created during use is focused at the face mask.

10. The BVM resuscitator of claim 1, wherein the rigid stabilizer bar is configured to prevent downward pressure applied to the rigid stabilizer bar in the plane of the rigid stabilizer bar from affecting one or more of the shape and functionality of the reservoir bag.

11. The BVM resuscitator of claim 1, wherein the rigid stabilizer bar is configured to enable normal and full compression of the reservoir bag when the reservoir bag is fully squeezed in a plane other than the plane of the rigid stabilizer bar.

12. The BVM resuscitator of claim 1, wherein the rigid stabilizer bar comprises:
    a stabilizer arm extending from the rigid connector toward a center of the reservoir bag;
    an extension extending at an upward angle from a body of the stabilizer arm; and
    a support lever disposed at a distal end of the extension and configured to receive a downward force in the plane of the rigid stabilizer bar.

13. The BVM resuscitator of claim 12, wherein the stabilizer arm extends the entire length of the reservoir bag.

14. The BVM resuscitator of claim 12, wherein the extension is coupled to the stabilizer arm via a hinge and is configured to articulate around the hinge.

15. The BVM resuscitator of claim 1, wherein the rigid stabilizer bar comprises a plurality of extension arm members.

16. The BVM resuscitator of claim 15, wherein at least one of the plurality of extension arm members extends along a top surface of the reservoir bag and another of the plurality of extension arm members extends along a bottom surface of the reservoir bag.

17. A method for operating a bag valve mask (BVM) resuscitator, the method comprising:
- positioning a face mask of the BVM resuscitator over a face of a patient;
- applying a downward force on a rigid stabilizer bar directly formed with and/or coupled to a hard plastic rigid connector and extending along a length of a reservoir bag of the BVM resuscitator, wherein the rigid stabilizer bar is configured to prevent one or more of compression, collapsing, and folding of the reservoir bag in a plane of the rigid stabilizer bar; and
- simultaneously squeezing the reservoir bag in a plane other than the plane of the rigid stabilizer bar, the reservoir bag being fully compressible in a plane other than the plane of the rigid stabilizer bar.

18. The method of claim 17, wherein the rigid connector forms a fulcrum for the rigid stabilizer bar that simultaneously:
- applies the downward force to the face mask to form a tight seal between the face mask and the patient's face, and
- prevents the downward force on the rigid stabilizer bar from affecting one or more of the shape and functionality of the reservoir bag.

* * * * *